US00PP26120P3

(12) United States Plant Patent
Clark

(10) Patent No.: US PP26,120 P3
(45) Date of Patent: Nov. 24, 2015

(54) BLACKBERRY PLANT NAMED 'OSAGE'

(50) Latin Name: ***Rubus* subgenus *Rubus* Watson**
Varietal Denomination: Osage

(71) Applicant: THE BOARD OF TRUSTEES OF THE UNIVERSITY OF ARKANSAS, Little Rock, AR (US)

(72) Inventor: John Reuben Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 97 days.

(21) Appl. No.: 13/987,214

(22) Filed: Jul. 11, 2013

(65) Prior Publication Data

US 2015/0020246 P1 Jan. 15, 2015

(51) Int. Cl.
*A01H 5/08* (2006.01)

(52) U.S. Cl.
USPC ..... Plt./203

(58) Field of Classification Search
USPC ..... Plt./203
CPC ..... A01H 5/0887
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark et al. |
| PP11,865 | P2 | 5/2001 | Clark et al. |
| PP14,935 | P2 | 6/2004 | Clark |
| PP15,788 | P2 | 6/2005 | Clark et al. |
| PP16,989 | P3 | 8/2006 | Clark et al. |
| PP17,162 | P3 | 10/2006 | Clark et al. |
| PP17,983 | P2 | 9/2007 | Cabrera Avalos |
| PP20,891 | P3 | 3/2010 | Clark |
| PP22,449 | P3 | 1/2012 | Clark |

OTHER PUBLICATIONS

University of Arkansas Blackberries, Osage blackberry overview, May 30, 2012.*
Ruple, A. et al., "An evaluation of fertility in Arkansas primocane-fruiting blackberries," (2010) Hort. Science 45:1-6.

* cited by examiner

*Primary Examiner* — Keith O. Robinson
(74) *Attorney, Agent, or Firm* — Andrus Intellectual Property Law, LLP

(57) ABSTRACT

Description and specifications of a new and distinct blackberry cultivar named 'Osage' which originated from seed produced by a hand pollinated cross of Ark. Selection 'A-1719T' (non-patented, unreleased genotype)×'A-2108T' (non-patented, unreleased genotype) is provided. This new blackberry cultivar can be distinguished by its excellent flavor, thornless canes, even drupelet fill and lack of white drupelets on berries, medium berry size, excellent postharvest storage potential, mid-early season ripening, high yields and healthy plants.

2 Drawing Sheets

Latin name: *Rubus* subgenus *Rubus* Watson.

BACKGROUND

The new floricane-fruiting cultivar of blackberry called 'Osage' is described herein. The new cultivar originated from a hand-pollinated cross of Arkansas selections 'A-1719'×'A-2108' made in 2000. The seeds resulting from this controlled hybridization were germinated in a greenhouse in the spring of 2001 and planted in a field near Clarksville, Ark. (West-Central Arkansas). The seedlings fruited in the summer of 2003 and one seedling, designated 'A-2362', was selected in 2003 for its excellent flavor, thornless canes, even drupelet fill and lack of white drupelets on berries, medium berry size, excellent postharvest storage potential, mid-early season ripening, high yields and healthy plants.

SUMMARY OF THE INVENTION

The new and distinct cultivar of blackberry originated from a hand-pollinated cross of Arkansas selections 'A-1719' (non-patented, unreleased genotype; female)×'A-2108' (non-patented, unreleased genotype; male) made in 2000 and located near Clarksville, Ark. (West-Central Arkansas). The botanical designation of the new cultivar of blackberry is *Rubus* subgenus *Rubus* Watson.

The seeds resulting from this controlled hybridization were germinated in a greenhouse in the winter to early spring of 2001 and planted in a field near Clarksville, Ark. The seedlings fruited in the summer of 2003 on floricanes and one seedling, designated 'A-2362', was selected in 2003 for its excellent flavor, thornless canes, even drupelet fill and lack of white drupelets on berries, medium berry size, excellent postharvest storage potential, mid-early season ripening, high yields and healthy plants.

During 2003, the original plant selection was propagated asexually from root cuttings at the above-noted location, and a test row of 20 plants was established. Subsequently, larger test plantings have been established with asexually multiplied plants at two locations in Arkansas.

The new cultivar has been asexually multiplied annually since 2003 by the use of root cuttings and by rooting adventitious shoots from root cuttings. It forms new shoots from adventitious buds on root cuttings readily. During all asexual multiplication, the characteristics of the original plant have been maintained and no aberrant phenotypes have appeared.

BRIEF DESCRIPTION OF THE PHOTOGRAPHS

The accompanying photographs show typical specimens of the new variety in color as nearly true as it is reasonably possible to make in a color illustration of this character. The plants shown in the figures are all three years old.

DETAILED DESCRIPTION OF THE NEW CULTIVAR 'OSAGE'

Figure 1:
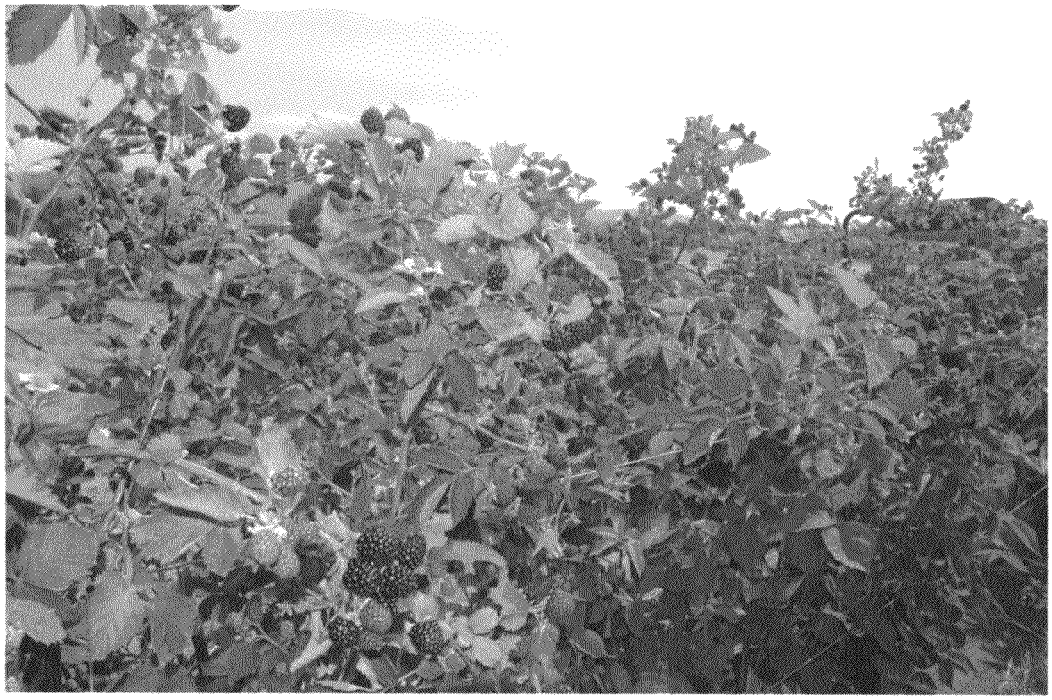
FIG. 1 is a photograph of blackberry canes of 'Osage' taken near Clarksville, Ark.
Figure 2:
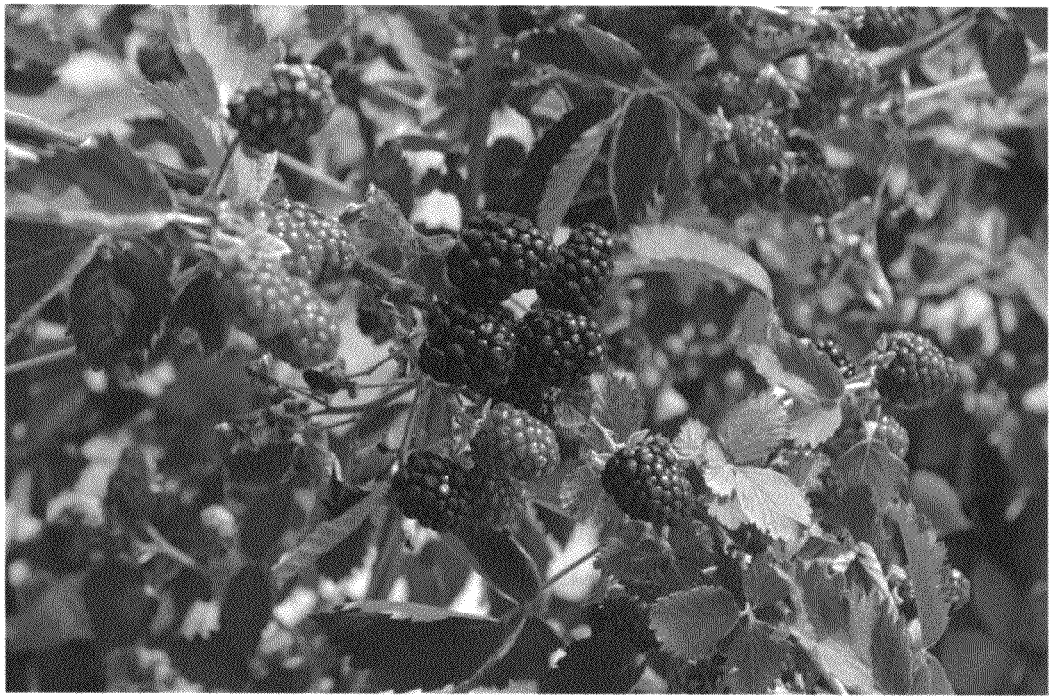
FIG. 2 is a photograph of ripe fruit on the plant of 'Osage'.
Figure 3:
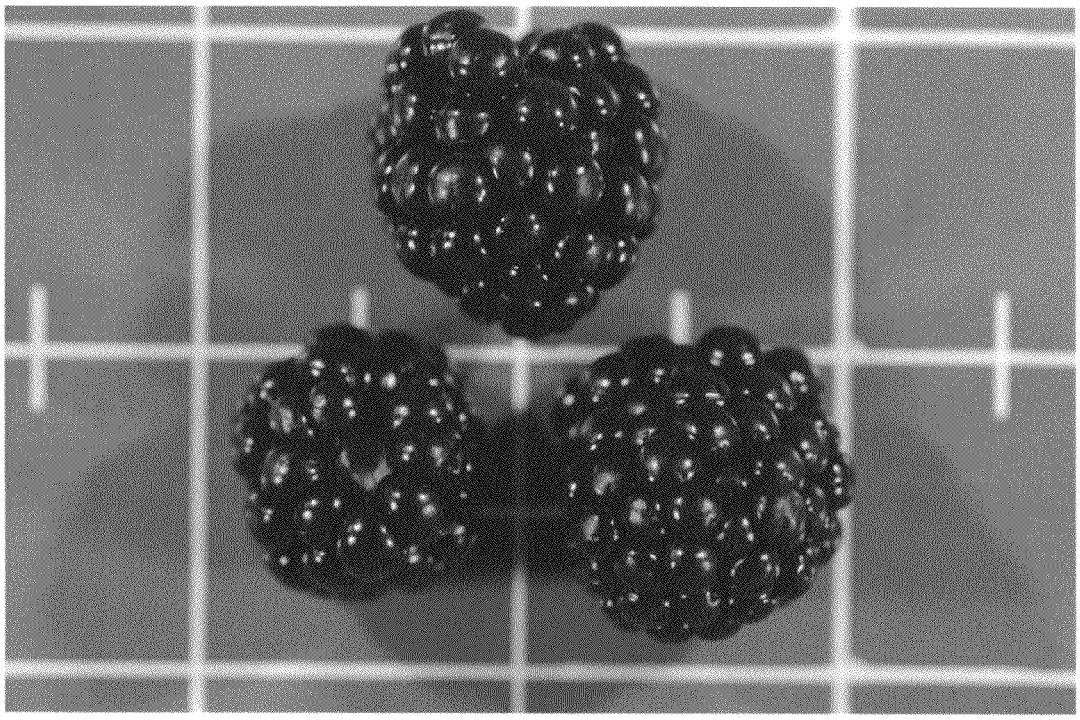
FIG. 3 is a photograph of ripe fruit of 'Osage'.
Figure 4:
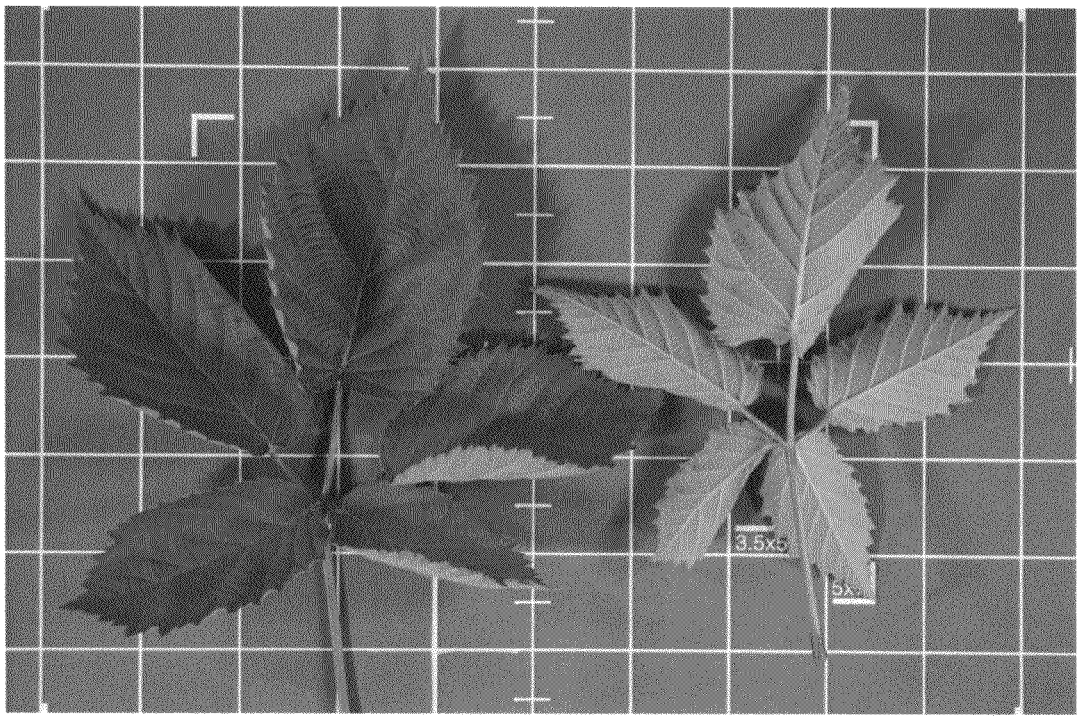
FIG. 4 is a photograph showing the abaxial and adaxial sides of a primocane leaf of 'Osage'.

Plants and fruit of this new cultivar differ phenotypically from its parents. The new cultivar is larger and more productive than its parent 'A-1719', and has better postharvest handling potential although slightly smaller berry than its parent 'A-2108'. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes can be trained to a self-supporting hedgerow although it is beneficial to use a trellis with supporting wires to prevent canes from falling over due to wind or heavy fruit loads. The plants are thornless. Plants and fruit are moderately resistant to anthracnose [*Elsinoe veneta* (Burkh.) Jenkins], and plants appear immune to orange rust [*Gymnoconia nitens* (Schwein.) F. Kern and H. W. Thurston.]. No screening has been done for resistance to double blossom/rosette [*Cercosporella rubi* (Wint.) Plakidas].

The bloom period of the new cultivar begins on average 26 April for 10% bloom and 2 May for 50% bloom. This is several days later than for 'Natchez' (U.S. Plant Pat. No. 20,891) and earlier than 'Ouachita' (U.S. Plant Pat. No. 17,162).

Fruit of the new cultivar has an average first harvest date of 10 June, 5 days after 'Natchez', and 3 days before 'Ouachita'. The average floricane fruiting period is 40 days.

Fruit yields of the new cultivar on floricanes are 3-4 kg (6-9 lb/plant), comparable to or exceeding that for 'Ouachita', in West-Central Arkansas.

The fruit is short, blocky, and uniform shape, bright glossy black in color, and very attractive. The floricane fruit is medium (5 g) and comparable to or slightly smaller than that of 'Ouachita'. Fruit size of the new cultivar is maintained well throughout the entire harvest season. The new cultivar exhibits excellent fruit fertility with full drupelet set. The fruit is very firm at maturity, comparable to that of 'Ouachita' and 'Natchez'. Storage potential of fresh fruit of the new cultivar is comparable to or exceeds that of 'Ouachita' and exceeds that of 'Natchez'.

The fresh fruit rates very good in flavor and is a major attribute of the cultivar, and is comparable to or exceeding that of 'Ouachita' and 'Natchez'. The flavor is sweet and mildly acidic, with a distinct blackberry aroma. The soluble solids concentration averages 10.3% on shiny black fruit, comparable to 'Natchez' and 'Ouachita'. Fruit and flower clusters are medium-large, cymose, and are mostly borne on the periphery of the plant canopy, providing easy access to harvest. Flower fertility is high and clusters are well filled.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with trickle irrigation at or near Clarksville, Ark. The plants were fertilized near budbreak (late March on average) with complete or nitrogen fertilizer, and had an additional nitrogen fertilizer application in early July. Primocanes were tipped at approximately 45 inches, and grown in a hedgerow training system. Weeds were controlled with pre- and postemergence herbicides supplemented with mechanical weed control activities. A single application of liquid lime sulfur was applied to the plants at budbreak, but no other fungicides were used. The descriptions reported herein are from specimens grown near Clarksville, Ark. unless otherwise noted.

Plant:

*Size*.—Plants are grown in a hedgerow and primocances tipped at approximately 45 inches; plants in this system then range in size from about 45 to 55 inches tall and approximately 24 inches wide at the top.

*Growth habit*.—Moderate vigor, canes erect; suckers from crown and roots.

*Growth rate*.—Primocanes 1$^{st}$ emergence is March 24 and primocanes reach tipping height (107 cm) on May 31.

*Productivity*.—Floricane — Slightly more than 3 kg (slightly over 6.5 lb/plant), comparable to 'Ouachita' and 'Natchez'.

*Cold hardiness*.—Hardy to 8° (−13° C.) or lower and comparable to Ouachita.

*Canes*.—Thornless, erect. Anthocyanin is present on the lateral canes, predominantly on the upper half of the canes. Floricane (dormant or winter cape): Cane diameter: base 2.09 cm; midpoint 1.73 cm; terminal 1.22 cm. Internode length: base 22.2 cm; midpoint 7.79 cm; terminal 7.58 cm. Floricane color: base Greyed-Orange Group (166A) and Yellow-Green Group (146C) (depending on side of cane and light exposure); midpoint Greyed-Orange Group (166A) and Yellow-Green Group (146C); terminus Greyed-Orange Group (166A) and Yellow-Green Group (146C). Thorn density (per 30 cm of cane length): plant is thornless. Primocane (current-season cane): Cane diameter: base 1.80 cm; midpoint 1.26 cm; terminal 0.66 cm. Internode length: base 9.12 cm; midpoint 5.60 cm; terminal 5.53 cm. Primocane color: base Green Group (140A) and Greyed-Purple Group (185A) depending on side of cane and light exposure; midpoint Green Group (141B); terminus Green Group (141B). Thorn density (per 30 cm of cane length): No thorns. Date of primocane emergence: 24 March.

*Disease resistance*.—Moderate resistant to anthracnose, and plants appear immune to orange rust. No screening has been done for resistance to double blossom/rosette.

Foliage:

*Primocane*.—Leaves: large; mature compound leaf width 23.82 cm; length 14.96 cm. Non-glossy upper side. Leaf bud burst in Clarksville, Ark. is March 8. Leaflet: Width 7.70 cm; length 9.33 cm; shape round to slightly elongate with acuminate apex and round to cordate base; margin doubly serrated, serration teeth length 0.36 cm and width 0.42 cm; pubescence is very light on abaxial and adaxial surfaces; number of leaflets per compound leaf: 5. Lobing of the terminal leaflet is absent. Color: Base abaxial Green Group (137C); adaxial Green Group (137A); midpoint abaxial Green Group (137D); adaxial Green Group (137A); terminal abaxial Green Group (137D); adaxial Green Group (137A). Petioles: Length: 9.24 cm; color: Green Group (139C) and Greyed-Red Group (181A); texture: moderately pubescent. Petiolules: Length: 2.72 cm; color: Green Group (139C) and Greyed-Red Group (181A); texture; moderately pubescent. Stipules; Length: 1.43 cm; width: 0.13 cm; texture: moderately pubescent.

*Floricane*.—Leaves: Large; mature compound leaf width 16.04 cm; length 11.67 cm. Non-glossy upper side. Leaflet: Width 9.15 cm; length 9.89 cm; shape ovate with acuminate apex and rounded base; margin bi-serrate, with serration teeth length 0.49 cm and width at base 0.39 cm; medium pubescence is present on abaxial side and light pubescence is present on the adaxial side. Number of leaflets per compound leaf is 3 most commonly but occasionally up to 5. Color: base abaxial Yellow-Green Group (146A); adaxial Green Group (139A); midpoint abaxial Green Group (141B); adaxial Green Group (137A); terminal abaxial Green Group (141B); adaxial Green Group (139A). Petioles: Length 2.14 cm; color: Yellow-Green Group (144B); texture: moderately pubescent. Petiolules: Length 0.27 cm; color: Yellow-Green Group (144B); texture: moderately pubescent. Stipules: Length 1.24 cm; width: 0.33 cm; texture: moderately pubescent.

Flowers:

*Floricane*.—Date of bloom: 26 April for 10% bloom and 2 May for 50% bloom in Clarksville, Ark. Petal color: Red Purple Group (65C) on both upper and lower surfaces.

*Reproductive organs*.—Stamens — erect, numerous. Pistils — numerous. Pollen — normal, fertile, and abundant.

*Flower diameter*.—3.42 cm.

*Petal size*.—Length 2.08 cm; width 1.70 cm.

*Average number flowers per cluster*.—5 to 6.

*Average number of petals per flower*.—5 to 9.

*Number of sepals per flower*.—5 to 6.

*Peduncle length*.—1.80 cm.

*Peduncle color*.—Yellow-Green Group (146D).

*Cyme type*.—Elongate simple cyme.

*Cyme length*.—12.7 cm.

Fruit:

*Floricane*.—Maturity — Average first ripe date 10 June, 5 days after 'Natchez' and 3 days before 'Ouachita'; with a fruiting period of 40 days. Size: Medium, average 5.0 g. Diameter of fruit at primary position on inflorescence: equator 2.23 cm; base pole 1.50 cm; terminal pole 0.80 cm. Diameter of fruit at secondary positions on inflorescence: equator 2.16 cm; base pole 1.37 cm; terminal pole 0.99 cm. Length (primary fruit): 2.48 cm. Shape: short, blocky, uniform. Color: Black Group (202A). Drupelet size: 0.51 cm; number per fruit 73. Seed: average length 3.14 mm; width 2.12 mm; dry weight 3.75 mg; color Orange White Group (159A). Soluble solids: 10.3%. pH: 3.21. Acidity: 0.46 g/100 ml expressed as citric acid. Processed quality: Not evaluated for processing. Uses: Fresh market use for shipping is the primary market due to excellent postharvest handling capability, but can also be used for other fresh market use including local sales.

The cultivar: The most distinctive features of the cultivar are its excellent flavor, thornless canes, even drupelet fill and lack of white drupelets on berries, medium berry size, excellent postharvest storage potential, mid-early season ripening, high yields and healthy plants.

I claim:

1. A new and distinct cultivar of blackberry plant named 'Osage,' substantially as illustrated and described herein.

* * * * *